United States Patent [19]

Pearce

[11] Patent Number: 4,717,398

[45] Date of Patent: Jan. 5, 1988

[54] SELECTIVE ADSORPTION AND RECOVERY OF ORGANIC GASES USING ION-EXCHANGED FAUJASITE

[75] Inventor: Graeme K. Pearce, Walkington, England

[73] Assignee: BP Chemicals Limited, London, England

[21] Appl. No.: 846,843

[22] Filed: Apr. 1, 1986

Related U.S. Application Data

[63] Continuation of Ser. No. 677,924, Dec. 4, 1984, abandoned.

[30] Foreign Application Priority Data

Dec. 30, 1983 [GB] United Kingdom ............... 8334610

[51] Int. Cl.$^4$ ............................................. B01D 53/04
[52] U.S. Cl. ........................................ 55/58; 55/68; 55/75
[58] Field of Search ............... 55/58, 68, 75, 389; 423/213.2, 247; 502/75, 79, 518

[56] References Cited

U.S. PATENT DOCUMENTS

| | | | |
|---|---|---|---|
| 2,254,799 | 9/1941 | Erdmann | 55/68 X |
| 2,978,407 | 4/1961 | Tuttle et al. | 55/75 X |
| 2,988,503 | 6/1961 | Milton et al. | 55/75 X |
| 3,346,328 | 10/1967 | Sergeys et al. | 423/213.2 |
| 3,476,508 | 11/1969 | Kearby et al. | 502/79 X |
| 3,497,462 | 2/1970 | Kruerke | 502/75 |
| 3,649,176 | 3/1972 | Rosback | 502/79 X |
| 3,649,177 | 3/1972 | Rosback | 502/79 X |
| 3,718,580 | 2/1973 | Rosback | |
| 3,720,604 | 3/1973 | Rosback | |
| 3,755,540 | 8/1973 | Rosback | 502/75 X |
| 3,789,106 | 1/1974 | Hay | 423/247 |
| 3,793,386 | 2/1974 | Davis | |
| 4,019,879 | 4/1977 | Rabo et al. | 55/68 |
| 4,034,065 | 7/1977 | Kasel et al. | 423/328 |
| 4,297,328 | 10/1981 | Ritscher et al. | 423/247 X |
| 4,331,644 | 5/1982 | Ritscher | 423/247 X |

FOREIGN PATENT DOCUMENTS

| | | | |
|---|---|---|---|
| 767066 | 11/1971 | Belgium . | |
| 555482 | 4/1958 | Canada | 55/75 |
| 2094476 | 4/1972 | France . | |
| 6702392 | 9/1968 | Netherlands . | |
| 1139405 | 1/1969 | United Kingdom | 55/75 |

OTHER PUBLICATIONS

Huang et al., "Cooper(I)-Ethylene Complexes in Y Zeolite", J.C.S., Chem. Comm., 1974, pp. 584, 585.
Huang, "Selective Adsorption of Carbon Monoxide and Complex Formation of Cuprous-Amines in Cu(I)Y Zeolites", J. of Cat. 30, 1973, pp. 187-194.
Su-842,461 (Abstract only) 6/30/1981.
Breck, "Zeolite Molecular Sieves, Structure, Chemistry and Use", 1974, pp. 176, 177 and 742-755, John Wiley & Sons Inc., publisher.
Breck, Zeolite Molecular Sieves, Structure, Chemistry, and Use, pp. 614, 715-717, 1974, John Wiley & Sons.
WO 8002558, Nov. 27, 1980, Thomas et al., Separating Ethane from Methane, 8 pages plus Search Report.

*Primary Examiner*—Robert Spitzer
*Attorney, Agent, or Firm*—Brooks Haidt Haffner & Delahunty

[57] ABSTRACT

This invention relates to a process for selectively adsorbing and recovering an organic gas containing unsaturated linkages from a mixture of gases over a cuprous ion-exchanged zeolite of the faujasite type. The process is particularly suited for adsorbing gases such as carbon monoxide and ethylene over a zeolite having a silica to alumina molar ratio from 1.5 to 3.0.

19 Claims, No Drawings

SELECTIVE ADSORPTION AND RECOVERY OF ORGANIC GASES USING ION-EXCHANGED FAUJASITE

This application is a continuation application of prior application Ser. No. 06/677,924, filed Dec. 4, 1984, and now abandoned.

The present invention relates to a process for selective adsorption and recovery of organic gases containing an unsaturated linkage such as alkenes or carbon monoxide from gaseous mixtures.

Several methods are known for the separation of carbon monoxide and alkenes from gaseous mixtures. These include, for instance, cryogenic distillation, liquid adsorption, membrane separation and the so called "pressure swing adsorption" in which adsorption occurs at a higher pressure than the pressure at which the adsorbent is regenerated. Of these methods, cryogenic distillation and liquid absorption are the more commonly used techniques for separating carbon monoxide and alkenes from gaseous mixtures containing molecules of similar size eg nitrogen or methane. However, both these methods have disadvantages such as high capital costs and high running costs. For instance, the liquid absorption method suffers from solvent loss and needs a complex solvent make-up and recovery system.

More recently, molecular sieves which can selectively adsorb carbon monoxide from gaseous mixtures by chemisorption have been investigated. Such methods are described in NL-A- No. 6702393, SU- No. 842461, U.S. Pat. No. 4,019,879 and U.S. Pat. No. 4,034,065. Of these the two U.S. patents refer to the use of high silica zeolites which have relatively high selectivities for carbon monoxide. However, these zeolites only have a moderate capacity for carbon monoxide and also require very low vacuum pressures to recover the adsorbed gases and to regenerate the zeolite.

Another publication which refers to the use of zeolites to adsorb gases is a paper by Huang, Y. Y. in the "Journal of Catalysis", Vol 30, pp 187-194 (1973), in which the adsorption capacity of a cuprous ion-exchanged zeolite Y system for several pure gases eg carbon monoxide is discussed. The system used has a good adsorption capacity for carbon monoxide but is said to require very low vacuum pressures for recovery of the adsorbed carbon monoxide and regeneration at ambient temperature.

The adsorption of pure ethylene on cuprous ion-exchange zeolite Y is also discussed by Huang and Mainwaring in J.C.S. Chem. Comm. 510, pp 584-585, 1974. Again strong complexes are said to be formed.

These phenomena are attributable to the high binding energy of the system used by Huang for carbon monoxide and alkenes. From the isotherms shown in FIG. 1 of the former paper by Huang, the recovery of carbon monoxide from the system when using a pressure swing of between 1 bar absolute and 10 m bar absolute at ambient temperature is expected to be low because the carbon monoxide is so strongly adsorbed.

Thus it appears that the system used by Huang adsorbs carbon monoxide much too strongly for it to be the basis of a commercially viable pressure swing recovery process at ambient temperatures.

Accordingly, the present invention is a process for selective adsorption and subsequent recovery of organic gases containing an unsaturated linkage from a mixture of gases by passing the mixture over a zeolite ion-exchanged with cuprous ions characterised in that the zeolite has a faujasite type structure and has a silicon to aluminium atomic ratio from 1.2–3.

By "organic gases containing an unsaturated linkage" is meant gases which have in their molecular structure a double or multiple covalent bond linking a carbon atom to another atom. Examples of such gases include carbon monoxide, an alkene or an alkyne. The process is particularly applicable to separation of carbon monoxide or alkenes such as ethylene from gaseous mixtures.

Zeolites of the faujasite type are described in standard texts including "Zeolite Molecular Sieves, Structure, Chemistry and Use" by Breck, D. W., pp 92/93, published by John Wiley & Sons Inc. (1974) and in "Molecular Sieve Zeolites-1", Advances in Chemistry Series 101, edited by Gould, R. F., pp 171 et seq. and published by the American Chemical Society (1971). These zeolites are classified to have an FAU-type structure as characterised by their X-ray diffraction pattern and listed in the book by Meier, W. M. and Olsen, D. H. entitled, "Atlas of Zeolite Structure Types", p 37, published by the Structure Commission of the International Zeolite Association (1978) and distributed by Polycrystal Book Service, Pittsburgh, Pa., USA.

Examples of the zeolites of the FAU-structure type that may be used include zeolites X and Y provided that they have a silicon to aluminium atomic ratio from 1.2 to 3. Zeolites having a silicon to aluminium ratio from 1.5–3, especially those having a ratio from 2 to 3, eg zeolite Y are preferred.

The zeolites used may be ion exchanged with cupric ions by any of the conventional techniques. For instance, a NaY zeolite may be exchanged initially by treatment with a cupric nitrate solution, washed, dried and then granulated with colloidal silica and then dried. The dried granulated zeolite containing cupric ions is then reduced to cuprous ion exchanged zeolite by passing carbon monoxide therethrough at elevated temperature. The resultant cuprous ion exchanged zeolite having a silicon to aluminium atomic ratio from 1.5 to 3 (hereafter termed "Cu(I)Y") is used for the selective adsorption of carbon monoxide from gaseous mixtures.

The ion-exchanged zeolites used in the present invention are capable of adsorbing gases either by chemisorption or by physisorption. In chemisorption the adsorbed gases are chemically bound to active sites on the zeolite whereas in physisorption the gases are only adsorbed physically in the pores and interstices of the zeolite. The process of the present invention is particularly suited for separating gases capable of chemisorption i.e. carbon monoxide and alkenes from gases capable only of physisorption i.e. hydrogen, argon, nitrogen and the lower paraffinic gases such as methane, ethane and propane.

The selective adsorption is suitably carried out by passing the gaseous mixture containing an organic gas with an unsaturated linkage over the cuprous ion-exchanged zeolite at ambient temperature eg 20° C. and pressure eg 1 bar absolute. The adsorbed carbon monoxide may be recovered and the cuprous ion-exchanged zeolite regenerated by applying a moderately low vacuum eg 10 m bar absolute at ambient temperature. For instance, using Cu(I)Y with a silicon to aluminium atomic ratio of 2.4, carbon monoxide was adsorbed from a 50/50 mixture thereof with nitrogen at 20° C. and 1 bar absolute. The adsorption capacity for carbon monoxide in this case was 1.3% w/w. The adsorbed gas contained approximately 97% w/w of carbon monoxide.

The adsorption regeneration cycle can be carried out between pressures of 1 m bar absolute and 40 bar absolute, preferably 10 m bar absolute and 20 bar absolute. The loading on the zeolite increases with the partial pressure of the adsorbed component. At 20 bar absolute the maximum adsorption capacity for CO of approximately 20 ml/gm is rapidly achieved. This corresponds to 1 mole of CO for every mole of cuprous ion exchanged onto the zeolite. Desorption occurs rapidly as the partial pressure of CO is reduced. Below 10 m bar absolute, the desorption rate becomes very slow.

Adsorption can be carried out in the temperature range −80° C. to 150° C., preferably −50° C. to +50° C. Loading is increased at lower temperatures whilst rapid adsorption and desorption rates are maintained.

It is preferable that the gaseous mixture being treated does not contain any combination of moisture and an oxidising agent such as moist air because of the risk of cuprous ions in the zeolite being oxidised to cupric ions.

It has been found that by using cuprous ion-exchanged zeolites of the faujasite type having a silicon to aluminium atomic ratio from 1.2 to 3.0, carbon dioxide is adsorbed and bound more strongly than carbon monoxide. This feature is in complete contrast to that observed by Huang, Y. Y. (loc. cit.) where carbon monoxide is more strongly bound than carbon dioxide.

The present invention is further illustrated with reference to the following Examples.

EXAMPLES

Details of Preparation of Cuprous Ion-Exchanged Zeolite

(a) Exchange

NaY zeolite which had a silicon to aluminium atomic ratio of 2.4 was exchanged with 0.2M $Cu(NO_3)_2$ at a concentration of 40 ml/gm of zeolite. The zeolite was filtered off, washed with water and dried. Analysis of this zeolite indicated that 60% of the Na+cation had been exchanged, giving a zeolite with 8.0% w/w copper.

(b) Granulation

The cupric ion-exchanged zeolite Y (hereafter termed "Cu(II)Y") produced in (a) above was granulated with colloidal silica by mixing in the following proportions; 7 gm Cu(II)Y, 10 gm water, 8 gm Ludox (Regd. Trade Mark) AS4 40% colloidal silica with the pH adjusted to 6 with M $HNO_3$. This mixture was slurried, dried at 100° C., and broken up on a 1 mm sieve to give granules of 1 to 1.5 mm. The silica content of the granules was 30% w/w. (Capacities are quoted on the basis of the total weight of zeolite plus binder).

(c) Reduction 10 g of the granulated Cu(II)Y produced in (b) above was pre-dried in a stream of $N_2$ at 450° C. with a flowrate of 30 ml/min for 6 hours. CO was then passed through the zeolite granules at the same flowrate for at least 3 hours with a temperature of 450° C. and at a pressure of 1.4 to 2 bar absolute to form the cuprous ion-exchanged zeolite Y (hereafter termed "Cu(I)Y") which was used in the following Examples.

EXAMPLE 1

Adsorption capacities and selectivities were measured at 20° C. and 1 bar absolute by passing single component binary gas mixtures over a Cu(I)Y bed containing helium at 1 bar absolute. The helium was displaced by the adsorbed gas with the capacity being indicated by volume difference and selectivity being inferred from compositional changes in the gas mixture before and after passage through the bed. In all the runs in this Example the bed of adsorbent was regenerated at 1 m bar absolute for 20 minutes. Single component capacities are listed in Table 1. Gases in Section A of Table 1 are the organic gases containing unsaturated linkages; these gases are chemisorbed by the Cu (I) Y and are selectively adsorbed from mixtures thereof with the physiosorbed gases listed in Section B of Table 1. Capacities and selectivities for various binary mixtures are given in Table 2.

EXAMPLE 2

The dependence of adsorption capacity on temperature was determined by passing a 70% w/w $CO/N_2$ feed at 1 bar absolute through a bed of Cu(I)Y at various temperatures and measuring the CO uptake. The bed was regenerated at 20 m bar absolute for 10 minutes. The results are shown in Table 3.

EXAMPLE 3

The adsorbed carbon monoxide from Example 2 was recovered and the cuprous ion-exchanged zeolite regenerated by applying moderately low vacuum pressures at ambient temperature. The extent of regeneration of the Cu(I)Y zeolite was measured as a function of vacuum pressure and time as shown in Table 4.

TABLE 1

Adsorption Capacities for Various Single Component Gases Relative to Helium

| Gas | Adsorption Capacity ml/gm |
|---|---|
| A. CHEMISORBED GASES | |
| CO | 13.0 |
| $C_2H_2$ | 26.8 |
| $C_2H_4$ | 33.0 |
| $C_3H_6$ | 29.3 |
| B. PHYSISORBED GASES | |
| $H_2$ | 0 |
| Ar | 1.5 |
| $N_2$ | 2.3 |
| $CH_4$ | 5.0 |
| $C_2H_6$ | 23.0 |
| $C_3H_8$ | 13.4 |

TABLE 2

Adsorption Selectivities for Various Binary Gas Mixtures

A. $CO/N_2$

| % v/v CO in feed gas | % v/v CO in adsorbed gas | CO adsorption ml/gm | $N_2$ adsorption ml/gm | Separation* Factor |
|---|---|---|---|---|
| 2.7 | 67 | 5.0 | 2.4 | 75 |
| 7.0 | 76 | 6.9 | 2.2 | 42 |
| 14.5 | 82 | 8.5 | 1.9 | 26 |
| 34.5 | 90 | 10.5 | 1.2 | 17 |
| 48.5 | 97 | 11.3 | 0.4 | 30 |

TABLE 2-continued

Adsorption Selectivities for Various Binary Gas Mixtures

| 62.5 | 98 | 11.9 | 0.2 | 36 |

B. CO/CH$_4$

| % v/v CO in feed gas | % v/v CO in adsorbed gas | CO adsorption ml/gm | CH$_4$ adsorption ml/gm | Separation Factor |
| --- | --- | --- | --- | --- |
| 21 | 57 | 6.6 | 4.9 | 5.1 |
| 40 | 70 | 8.5 | 3.7 | 3.5 |
| 56 | 79 | 8.6 | 2.3 | 2.9 |

C. C$_2$H$_4$/CH$_4$

| % v/v C$_2$H$_4$ in feed gas | % v/v C$_2$H$_4$ in adsorbed gas | C$_2$H$_4$ adsorption ml/gm | CH$_4$ adsorption ml/gm | Separation Factor |
| --- | --- | --- | --- | --- |
| 50 | 99 | 21.7 | 0.1 | 217 |

D. C$_2$H$_4$/C$_2$H$_6$

| % v/v C$_2$H$_4$ in feed gas | % v/v C$_2$H$_4$ in adsorbed gas | C$_2$H$_4$ adsorption ml/gm | C$_2$H$_6$ adsorption ml/gm | Separation Factor |
| --- | --- | --- | --- | --- |
| 22 | 44 | 11.1 | 14.0 | 2.8 |
| 56 | 79 | 22.8 | 6.2 | 2.9 |

E. C$_3$H$_6$/C$_3$H$_8$

| % v/v C$_3$H$_6$ in feed gas | % v/v C$_3$H$_6$ in adsorbed gas | C$_3$H$_6$ adsorption ml/gm | C$_3$H$_8$ adsorption ml/gm | Separation Factor |
| --- | --- | --- | --- | --- |
| 24 | 40 | 6.1 | 9.3 | 2.1 |
| 53 | 81 | 14.4 | 3.4 | 3.8 |

*Separation factor (CO:N$_2$) = $\frac{[CO]\ ads}{[N_2]\ ads} \cdot \frac{[N_2]\ feed}{[CO]\ feed}$

TABLE 3

| Temperature °C. | CO Adsorption Capacity, ml/gm |
| --- | --- |
| −23 | 9.4 |
| 25 | 7.2 |
| 95 | 3.5 |

TABLE 4

Effect of Regeneration Conditions on CO Adsorption
(Capacities expressed as % of fully regenerated capacity at 10 m bar A)

| Regeneration Pressure mbarA | Regeneration Time, minutes | | | | |
| --- | --- | --- | --- | --- | --- |
|  | 1 | 2 | 5 | 10 | 20 |
| 10 | 52 | 64 | 76 | 84 | 92 |
| 50 | 44 | 55 | 64 | 69 | 75 |
| 100 | 41 | 48 | 55 | 60 | 63 |

I claim:

1. A pressure swing process for selectively absorbing and recovering an organic gas containing unsaturated linkages from a mixture of gases by passing the mixture over a zeolite ion-exchanged with cuprous ions characterized in that the zeolite has a faujasite type structure and has a silicon to aluminum atomic ratio from 1.2–3 and wherein the zeolite has been granulated after being copper ion-exchanged and prior to contact with the gaseous mixture.

2. A process according to claim 1 wherein the gas containing unsaturated linkages is selected from carbon monoxide and an alkene.

3. A process according to claim 2 wherein the alkene is ethylene.

4. A process according to claim 1 wherein the zeolite has a silicon to aluminum atomic ratio from 2–3.

5. A process according to claim 1 wherein the selective adsorption is carried out by passing the gaseous mixture over the zeolite at ambient temperature and pressure.

6. A process according to claim 1 for adsorbing from a gaseous mixture an organic gas containing unsaturated linkages over a zeolite wherein the adsorbed organic gas is recovered and the cuprous ion-exchanged zeolite regenerated by applying a low vacuum at ambient temperature.

7. A pressure-swing process as defined in claim 1 wherein said granulated zeolite has a particle size greater than 1 mm.

8. The process of claim 1, wherein the mixture of gases essentially consists of carbon monoxide and nitrogen.

9. The process of claim 1, wherein the mixture of gases essentially consists of carbon monoxide and methane.

10. The process of claim 1, wherein the mixture of gases essentially consists of ethylene and methane.

11. The process of claim 1, wherein the mixture of gases essentially consists of ethylene and ethane.

12. The process of claim 1, wherein the mixture of gases essentially consists of propylene and propane.

13. A pressure swing process for selectively absorbing and recovering an organic gas containing unsaturated linkages from a mixture of gases by passing the mixture over a zeolite ion-exchanged with cuprous ions, characterised in that the zeolite has a faujasite type structure and has a silicon to aluminum atomic ratio from 1.2–3; and
wherein the zeolite is prepared by the following series of steps:
initially exchanging the zeolite by treatment with cupric ions,
granulating the initially exchanged zeolite so that the granulated zeolite has a particle size greater than 1 mm, and
reducing the granulated zeolite containing cupric ions to said cuprous ion exchanged zeolite,
prior to contact with the gaseous mixture.

14. The process according to claim 13, wherein the granulated zeolite has a particle size of 1 to 1.5 mm.

15. The process of claim 13, wherein the mixture of gases essentially consists of carbon monoxide and nitrogen.

16. The process of claim 13, wherein the mixture of gases essentially consists of carbon monoxide and methane.

17. The process of claim 13, wherein the mixture of gases essentially consists of ethylene and methane.

18. The process of claim 13, wherein the mixture of gases essentially consists of ethylene and ethane.

19. The process of claim 13, wherein the mixture of gases essentially consists of propylene and propane.

* * * * *